US006110463A

United States Patent [19]
Riggs et al.

[11] Patent Number: 6,110,463
[45] Date of Patent: Aug. 29, 2000

[54] ANTI-*CRYPTOSPORIDIUM PARVUM* PREPARATIONS

[75] Inventors: Michael W. Riggs, Tucson, Ariz.; Lance E. Perryman, Cary, N.C.

[73] Assignees: North Carolina State University, Raleigh, N.C.; The Arizona Board of Regents, Tucson, Ariz.

[21] Appl. No.: 08/828,943

[22] Filed: Mar. 27, 1997

Related U.S. Application Data

[60] Provisional application No. 60/014,410, Mar. 29, 1996, and provisional application No. 60/021,465, Jul. 10, 1996.

[51] Int. Cl.$^7$ .................. A61K 39/395; A61K 35/20; C07K 16/20; C12N 5/20

[52] U.S. Cl. .................. 424/151.1; 424/535; 424/807; 435/7.22; 435/70.21; 435/172.2; 435/342; 530/388.6; 530/822; 530/832

[58] Field of Search .................. 424/130.1, 151.1, 424/265.1, 266.1, 269.1, 535, 807; 435/7.22, 70.21, 172.2, 947, 342; 530/388.6, 389.1, 822, 832; 935/104, 107, 108

[56] References Cited

PUBLICATIONS

Riggs, M.W., Yount, P.A., Stone, A.L., Langer, R.C. (1996) Protective Monoclonal Antibodies Define a Distinct, Conserved Epitope on an Apical Complex Exoantigen of *Cryptosporidium parvum* Sporozoites. J. Euk. Microbiol. 43:74S–75S.

Langer, R.C., Riggs, M.W. (1996) Neutralizing Monoclonal Antibody Protects Against *Cryptosporidium parvum* Infection by Inhibiting Sporozoite Attachment and Invasion. J. Euk. Microbiol. 43:76S–77S.

Albert, M.M., Rusnak, J., Luther, M.F. and Graybill, J.R. (1994) Treatment of murine cryptosporidiosis with anti–cryptosporidial immune rat bile. Am. J. Trop. Med. Hyg., 50:112.

Arrowood, M.J., Mead, J.R., Mahrt, J.L. and Sterling, C.R. (1989) Effects of immune colostrum and orally administered antisporozoite monoclonal antibodies on the outcome of *Cryptosporidium parvum* infections in neonatal mice. Infect. Immun., 57:2283.

Arrowood, M.J., Sterling, C.R. and Healey, M.C. (1991) Immunofluorescent microscopical visualization of trails left by gliding *Cryptosporidium parvum* sporozoites. Parasitol., 77:315–317.

Bjorneby, J.M. Riggs, M.W. and Perryman, L.E. (1990) *Cryptosporidium parvum* merozoites share neutralization–sensitive epitopes with sporozoites. J. Immunol., 145:298–304.

Bjorneby, J.M., Hunsaker, B.D., Riggs, M.W. and Perryman, L.E. (1991) Monoclonal antibody immunotherapy in nude mice persistently infected with *Cryptosporidium parvum*. Infect. Immun., 59:1172.

Bonnin, A., Dubremetz, J.F. and Camerlynck, P. (1991) Characterization of microneme antigens of *Cryptosporidium parvum*. Infect. Immun., 59:1703.

Bonnin, A., Dubremetz, J.F. and Camerlynck, P. (1993) A new antigen of *Cryptosporidium parvum* micronemes possessing epitopes cross–reactive with macrogamete granules. Parasitol. Res., 79:8–14.

Bonnin, A., Gut, J., Dubremetz, J.F., Newlson, R. and Camerlynck, P. (1995) Monoclonal antibodies identify a subset of dense granules in *Cryptosporidium parvum* zoites and gamonts. J. Euk. Microbiol., 42:395.

Borowitz, S.M. and Saulsbury, F.T. (1991) Treatment of chronic cryptosporidial infection with orally administered human serum immune globulin. J. Pediatrics, 119:593.

Cama, V.A. and Sterling, C.R. (1991) Hyperimmune hens as a novel source of anti–Cryptosporidium antibodies suitable for passive immune transfer. J. Protozool., 38:42S.

Cho, M.–H. (1993) Passive transfer of immunity against Cryptosporidium infection in neonatal mice using monoclonal antibodies. Kor. J. Parasitol., 31:223–30.

Cochrane, A.H., Aikawa, M., Jeng, M. and Nussenzweig, R.S. (1976) Antibody–induced ultrastructural changes of malarial sporozoites. J. Immunol., 116:859.

Doyle, P.S., Crabb, J. and Petersen, C. (1993) Anti–*Cryptosporidium parvum* antibodies inhibit infectivity in vitro and in vivo. Infect. Immun., 61:4079.

Fayer, R., Perryman, L.E. and Riggs, M.W. (1989) Hyperimmune bovine colostrum neutralizes Cryptosporidium sporozoites and protects mice against oocyst challenge. J. Parasitol., 75:151.

Fayer, R., Andrews, C., Ungar, B.L.P. and Blagburn, B. (1989) Efficacy of hyperimmune bovine colostrum for prophylaxis of cryptosporidiosis in neonatal calves. J. Parasitol., 75:393.

Fayer, R. Guidry, A. and Blagburn, B.L. (1990) Immunotherapeutic efficacy of bovine colostral immunoglobulins from a hyperimmunized cow against cryptosporidiosis in neonatal mice. Infect. Immun., 58:2962.

Fayer, R., Tilley, M., Upton, S.J., Guidry, A.J., Thayer, D.W., Hildreth, M. and Thomson, S. (1991) Production and preparation of hyperimmune bovine colostrum for passive immunotherapy of cryptosporidiosis. J. Protozool., 38:38S.

(List continued on next page.)

*Primary Examiner*—Christopher L. Chin
*Assistant Examiner*—James L. Grun
*Attorney, Agent, or Firm*—Oblon, Spivak, McClelland, Maier & Neustadt, P.C.

[57] ABSTRACT

Compositions and methods useful for conferring passive or active immunity to the parasite, *C. parvum*. A high molecular weight glycoprotein antigen isolated from *C. parvum*, capable of binding the mAb 3E2, was shown to harbor an epitope critical for triggering the neutralizing CSP-like reaction in the parasite. Antibodies targeted against the critical epitope were shown to possess neutralizing activity, and could be combined with other anti-*C. parvum* monoclonal antibodies and administered to an animal to confer passive immunity. Immunogenic compositions including the purified antigen are disclosed for use in stimulating an active immune response against *C. parvum*.

23 Claims, No Drawings

OTHER PUBLICATIONS

Flanigan, T., Marshall, R., Redman, D., Kaetzel, C. and Ungar, B. (1991) In vitro screening of therapeutic agents against Cryptosporidium: hyperimmune cow colostrum is highly inhibitory. J. Protozool., 38:225S.

Flanigan, T.P. (1994) Human immunodeficiency virus infection and cryptosporidiosis: protective immune responses. Am. J. Trop. Med. Hyg., 50:29.

Flanigan, T.P., Wisnewski, A., Wiest, P.M., Johnson, J., Tzipori, S., Hamer, D., Lam, N. and Kresina, T.F. (1993) Human monoclonal antibodies against *Cryptosporidium parvum* generated by hypo–osmolar electrofusion. Trans. Assoc. Am. Phys. 106:86–90.

Gut, J. and Nelson, R.G. (1994) *Cryptosporidium parvum* sporozoites deposit trails of 11A5 antigen during gliding locomotion an shed 11A5 antigen during invasion of MDCK cells in vitro. J. Euk. Microbiol., 41:42S.

Harp, J.A. and Goff, J.P. (1995) Protection of calves with a vaccine against *Cryptosporidium parvum*. J. Parasitol., 81:54–7.

Hill, B.D., Dawson, A.M. and Blewett, D.A. (1993) Neutralisation of *Cryptosporidium parvum* sporozoites by immunoglobulin and nonimmunoglobulin components in serum. Res. Vet. Sci., 54:356.

Jenkins, M., Kerr, D., Fayer, R. and Wall, R. (1996) Serum and colostrum antibody responses induced by jet–injection of sheep with DNA encoding a *Cryptosporidium parvum* antigen. Vaccine. 13:1658–64.

Kuhls, T.L., Orlicek, S.L., Mosier, D.A., Crawford, D.L., Abrams, V.L. and Greenfield, R.A. (1995) Enteral human serum immunoglobulin treatment of cryptosporidiosis in mice with severe combined immunodeficiency. Infect. Immun., 63:3582–6.

Luft, B.J. Payne, D., Woodmansee, D. and Kim, C.W. (1987) Characterization of the Cryptosporidium antigens from sporulated oocysts of *Cryptosporidium parvum*. Infect. Immun., 55:2436.

McDonald, V., Deer, R.M.A., Nina, J.M.S., Wright, S., Chiodini, P.L. and McAdam, K.P.W.J. (1991) Characteristics and specificity of hybridoma antibodies against oocyst antigens of *Cryptosporidium parvum* from man. Parasite Immunol., 13:251.

McDonald, V., McCrossan, M.V. and Petry, F. (1995) Localization of parasite antigens in *Cryptosporidium parvum* infected epithelial cells using monoclonal antibodies. Parasitol., 110:259.

Mead, J.R., Arrowood, M.J. and Sterling, C.R. (1988) Antigens of Cryptosporidium sporozoites recognized by immune sera of infected animals and humans. J. Parasitol., 74:135–143.

Naciri, M. Mancassola, R. Reperant, J.M., Canivez, O., Quinique, B. and Yvore, P. (1994) Treatment of experimental ovine cryptosporidiosis with ovine and bovine hyperimmune colostrum. Vet. Parasitol., 53:173.

Nina, J.M.S., McDonald, V., Deer, R.M.A., Wright, S.E., Dyson, D.A., Chiodini, P.L. and McAdam, K.P.W.J. (1992) Comparative study of the antigenic composition of oocyst isolates of *Cryptosporidium parvum* from different hosts. Parasite Immunol., 14:227.

Nord, J., Ma, P., DiJohn, D., Tzipori, S. and Tacket, C.O. (1990) Treatment with bovine hyperimmune colostrum of cryptosporidial diarrhea in AIDS patients. AIDS. 4:581–4.

Perryman, L.E., Riggs, M.W., Mason, P.H. and Fayer, R. (1990) Kinetics of *Cryptosporidium parvum* sporozoite neutralization by monoclonal antibodies, immune bovine serum, and immune bovine colostrum. Infect. Immun., 58:257.

Perryman, L.E. and Bjorneby, J.M. (1991) Immunotherapy of cryptosporidiosis in immunodeficient animal models. J. Protozool, 38:98S.

Perryman, L.E., Kegerreis, K.A. and Mason, P.H. (1993) Effect of orally administered monoclonal antibody on persistent *Cryptosporidium parvum* infection in SCID mice. Infect. Immun., 61:4906–8.

Perryman, L.E., Jasmer, D.P., Riggs, M.W., Bohnet, S.G., McGuire, T.C. and Arrowood, M.J. (1996) A cloned gene of *Cryptosporidium parvum* encodes neutralization–sensitive epitopes. Mol. Biochem. Parasitol., 80:137–47.

Petersen, C., Gut, J., Nelson, R.G. and Leech, J.H. (1991) Characteristics of a *Cryptosporidium parvum* sporozoite glycoprotein, J. Protozool., 38:20S.

Petersen, C., Gut, J., Doyle, P.S., Crabb, J.H., Nelson, R.G. and Leech, J.H. (1992) Characterization of a <900,000–M(r) *Cryptosporidium parvum* sporozoite glycoprotein recognized by protective hyperimmune bovine colostral immunoglobulin. Infect. Immun., 60:5132.

Plettenberg, A., Stoehr, A., Stellbrink, H.J., Albrecht, H. and Meigel, W. (1993) A preparation from bovine colostrum in the treatment of HIV–positive patients with chronic diarrhea. Clin. Invest., 71:42–5.

Regan, S., Cama, V. and Sterling, C.R. (1991) Cryptosporidium merozoite isolation and purification using differential centrifugation techniques. J. Protozool., 38:202S.

Riggs, M.W. and Perryman, L.E. (1987) Infectivity and neutralization of *Cryptosporidium parvum* sporozoites. Infect. Immun., 55:2081.

Riggs, M.W., McGuire, T.C., Mason, P.H. and Perryman, L.E. (1989) Neutralization–sensitive epitopes are exposed on the surface of infectious *Cryptosporidium parvum* sporozoites. J. Immunol., 143:1340–5.

Riggs, M.W., Cama, V.A., Leary, H.L., Jr. and Sterling, C.R. (1994) Bovine antibody against *Cryptosporidium parvum* elicits a circumsporozoite precipitate–like reaction and had immunotherapeutic effect against persistent cryptosporodiosis in SCID mice. Infect. Immun., 62:1927–1939.

Riggs, M.W., Stone, A.L., Arrowood, M.J., Langer, R.C., Bahle, J. and Yount, P. (1994) Molecular targets for passive immunotherapy of cryptosporidiosis. Proc. 47th Annual Meeting of the Society of Protozoologists and 3rd Int. Workshop on Pneumocystis, Toxoplasma, Cryptosporidium and Microsporidia: Abstract C46:76.

Riggs, M.W. (1997) Protective Monoclonal Antibody Defines a Circumsporozoite–Like Glycoprotein Exoantigen of *Cryptosporidium parvum* Sporozoites and Merozoites. The Journal of Immunology:1787–1795.

Robert, B., Antoine, H., Dreze, F., Coppe, P. and Collard, A. (1994) Characterization of a high molecular weight antigen of *Cryptosporidium parvum* micronemes possessing epitopes that are cross–reactive with all parasitic life–cycle stages. Vet. Res., 25:384.

Shield, J., Melville, C., Novelli, V., Anderson, G., Scheimberg, I., Gibb, D. and Milla, P. (1993) Bovine colostrum immunoglobulin concentrate for cryptosporidiosis in AIDS. Arch. Dis. Child., 69:451.

Tatalick, L.M. and Perryman, L.E. (1995) Attempts to protect severe combined immunodeficient (SCID) mice with antibody enriched for reactivity to *Cryptosporidium parvum* surface antigen–1. Vet. Parasitol., 58:281.

Tilley, M. Fayer, R., Guidry, A., Upton, S.J. and Blagburn, B.L. (1990) *Cryptosporidium parvum* (Apicomplexa: Cryptosporidiidae) oocyst and sporozoite antigens recognized by bovine colostral antibodies. Infect. Immun., 58:2966–71.

Tilley, M., Upton, S.J., Fayer, R., Barta, J.R., Chrisp, C.E., Freed, P.S., Blagburn, B.L., Anderson, B.C. and Barnard, S.M. (1991) Identification of a 15–kilodalton surface glycoprotein on sporozoites of *Cryptosporidium parvum*. Infect. Immun., 59:1002.

Tilley, M. and Upton, S.J. (1991) Sporozoites and merozoites of *Cryptosporidium parvum* share a common epitope recognized by a monoclonal antibody and two–dimensional electrophoresis. J. Protozool., 38:48S.

Tilley, M., Eggleston, M.T. and Upton, S.J. (1993) Multiple oral inoculations with *Cryptosporidium parvum* as a means of immunization for production of monoclonal antibodies. FEMS Microbiol. Lett., 113:235.

Tilley, M. and Upton, S.J. (1994) Both CP15 and CP25 are left as trails behind gliding sporozoites of *Cryptosporidium parvum* (Apicomplexa). FEMS Microbiol. Lett., 120:275–8.

Tzipori, S., Roberton, D. and Chapman, C. (1986) Remission of diarrheoa due to cryptosporidiosis in an immunodeficient child treated with hyperimmune bovine colostrum. Br. Med. J., 293:1277.

Tzipori, S., Roberton, D., Cooper, D.A. and White, L. (1987) Chronic cryptosporidial diarrhoea and hyperimmune cow colostrum. Lancet, 2:344.

Tzipori, S., Rand, W., Griffiths, J., Widmer, G. and Crabb J. (1994) Evaluation of an animal model system for cryptosporidiosis: therapeutic efficacy of paromomycin and hyperimmune bovine colostrum–immunoglobulin. Clin. Diag. Lab. Immunol, 1:450.

Uhl, E.W., O'Connor, R.M., Perryman, L.E. and Rigs, M.W. (1992) Neutralization–sensitive epitopes are conserved among geographically diverse isolates of *Cryptosporidium parvum*. Infect. Immun., 60:1703.

Ungar, B.L., Ward, D.J., Fayer, R. and Quinn, C.A. (1990) Cessation of Cryptosporidium–associated diarrhea in and Acquired Immunodeficiency Syndrome patient after treatment with hyperimmune bovine colostrum. Gastroenterology, 98:486–9.

Watzl, B., Huang, D.S., Alak, J., Darban, H., Jenkins, E.M. and Watson, R.R. (1993) Enhancement of resistance to *Cryptosporidium parvum* by pooled bovine colostrum during murine retroviral infection. Am. J. Trop. Med. Hyg., 48:519.

ANTI-*CRYPTOSPORIDIUM PARVUM* PREPARATIONS

RELATED APPLICATION

This application claims the benefit of priority under 35 U.S.C. § 119(e) of the U.S. provisional patent applications having serial numbers 60/014,410, filed Mar. 29, 1996, and Ser. No. 60/021,465, filed Jul. 10, 1996.

GOVERNMENT INTEREST IN THE INVENTION

Certain aspects of the invention disclosed herein were made with United States government support under Public Health Service (NIH), Government Contract No. U01 A1 30223; USDA Special Grant, Contract No. 89-34116-4550; and USDA NRICGP, Contract No. 94-37204-0496. The United States government has certain rights in these aspects of the invention.

FIELD OF THE INVENTION

The present invention relates to preparations useful for conferring passive or active immunity to the parasite, *Cryptosporidium parvum*. More specifically, the invention relates to a purified glycoprotein constituent of the parasite; use of the glycoprotein in an immunogenic composition; and monoclonal antibodies that bind a particular epitope disposed on the glycoprotein.

BACKGROUND OF THE INVENTION

*Cryptosporidium parvum* is a coccidian parasite that causes intestinal disease in humans as well as economically important food animals including calves, lambs, and goat kids. Healthy, immunocompetent adult humans can be infected, but cryptosporidiosis is particularly serious when it occurs in immunodeficient individuals, including neonates, and those who are immunocompromised as a result of medical treatment, or because of other disease, such as infection by human immunodeficiency virus (HIV).

Among domestic animals, cryptosporidiosis is most frequently reported in calves. The ubiquity of *C. parvum* in dairy and beef operations throughout the U.S. and its importance as a cause of calf diarrhea are well documented. For example, Anderson et al. in *Vet. Med. Sm. Anim. Clin.* (June 1981) described well-managed, closed-herd dairies in which *C. parvum*-related morbidity in 1–2 week old calves approached 100%. We conservatively estimate that the combined treatment costs and decreased production losses incurred by the U.S. cattle industry due to cryptosporidiosis alone now exceed $50,000,000 each year.

*C. parvum* infection begins when sporozoites released from ingested oocysts invade intestinal epithelial cells. Following attachment of the anterior pole of sporozoites to intestinal epithelium, invasion is associated with host cell membrane evagination around the sporozoite and parasitophorous vacuole formation. Vacuole formation in the apical complex of invading sporozoites is thought to represent discharge of invasion mediators from apical organelles. Following invasion, a feeder organelle forms between the parasite and the host cell cytoplasm and increases the interface surface area markedly. This organelle may function in transport of materials between the host cell and developing trophozoite. Two stages of merogony follow trophozoite development. Type 1 merozoites undergo cyclic replication before developing into type 2 merozoites. Type 2 merozoites subsequently give rise to sexual stages. Fertilization follows and results in the production of oocysts which are sporulate at the time of passage in feces. Autoinfective sporozoite and merozoite loops in the life cycle may perpetuate infection in immunocompromised hosts.

Since the first cases of human cryptosporidiosis were reported in 1976, Cryptosporidium has become recognized as a common cause of diarrhea in international travelers, children in day-care centers, livestock handlers, and patients with AIDS or other immune deficiency disorders. Among several recent studies that have addressed the prevalence of *C. parvum* infection in AIDS patients with diarrhea, one study identified Cryptosporidium as the most common enteropathogen in diarrheic AIDS patients (Laughon et al. *Gastroenterol.* 94:984 (1988)). Dissemination to extraintestinal sites such as the esophagus, lungs, pancreas and liver has also been shown to occur in immune deficient patients (Soave et al. *Rev. Inf. Dis.* 8:1012 (1986); Ungar et al. "Cryptosporidiosis in Humans" pp. 67–75, in J P Dubey, C A Speer and R Fayer (eds.), *Cryptosporidiosis of Man and Animals*, CRC Press (1990)).

Unlike the other major causes of diarrhea, including infection by *E. coli*, rotavirus and coronavirus, there are no effective control measures available for cryptosporidiosis. Despite the evaluation of more than 90 drugs, none has been of consistent value and no immunization regimen is presently available to protect against infection by *C. parvum*. Control of *C. parvum* infection therefore depends on achieving an adequate immune response. An index of adequate response comprises resistance to reinfection following recovery and short-term disease in immunocompetent hosts. The disease may persist however in immunodeficient hosts.

While cell-mediated immunity is important to naturally occurring resistance to many coccidial species, the evidence suggests that antibody responses can also be manipulated to control infection with sporozoan parasites. For example, hyperimmune bovine serum or colostral whey against whole *C. parvum* neutralized sporozoite infectivity and partially protected mice and calves against oocyst challenge. Additionally, oral administration of hyperimmune bovine colostrum to persistently infected immunodeficient patients was followed by cessation of diarrhea and oocyst shedding. Further, monoclonal antibodies (mAbs) reactive with *C. parvum* sporozoite and merozoite surface epitopes neutralized their infectivity and partially protected mice against oocyst challenge.

SUMMARY OF THE INVENTION

According to a first aspect of the invention there is provided a monoclonal antibody having the epitope binding specificity of antibody 3E2. In one embodiment, the monoclonal antibody and antibody 3E2 compete with each other for binding to an antigen that is present in a preparation solubilized *C. parvum* sporozoites. This monoclonal antibody, which competes with antibody 3E2 for antigen binding, stimulates a circumsporozoite precipitate-like (CSP-like) reaction after contacting *C. parvum* sporozoites. According to a different embodiment, the monoclonal antibody can have an IgM isotype. In a particular case, the monoclonal antibody is antibody 3E2. The invention also provides a hybridoma that secretes the monoclonal antibody 3E2.

According to a second aspect of the invention there is provided a pharmaceutical composition for administration to a mammal, comprising a monoclonal antibody secreted by hybridoma 3E2 and a pharmaceutically acceptable carrier. The invented composition also can include at least one monoclonal antibody other than the monoclonal antibody secreted by hybridoma 3E2. In a preferred embodiment, this other monoclonal antibody has an epitope binding specificity different from the binding specificity of the monoclonal antibody secreted by hybridoma 3E2. The carrier of the pharmaceutical composition can include at least one stabilizing agent which may be a protease inhibitor, a carrier protein or a pH buffering agent. In one embodiment, the carrier optionally comprises colostrum, for example, bovine colostrum.

A third aspect of the invention relates to a method of providing to a mammal passive immunity against *C. parvum* infection, comprising the step of administering to the mammal a composition comprising antibody 3E2, thereby providing passive immunity. In one embodiment, the composition administered to the mammal comprises a *C. parvum* neutralizing amount of monoclonal antibody 3E2. According to a different embodiment, the administered composition includes at least one monoclonal antibody other than antibody 3E2 that specifically binds a *C. parvum* antigen. In a preferred method the composition comprising antibody 3E2 is administered orally in the administering step. In another preferred embodiment of the method, the mammal is a human and in a particularly preferred embodiment the mammal is an immunocompromised human.

A fourth aspect of the invention relates to an isolated circumsporozoite-like antigen of *C. parvum* which includes a glycoprotein having a molecular weight of 1,400 kDa and which harbors an epitope specifically recognizable by monoclonal antibody 3E2. The isolated antigen can be isolated by a method that includes centrifugation, more particularly, density gradient centrifugation. Alternatively, the isolated antigen can be isolated by methods that involve immunoprecipitation, isoelectric focusing or preparative polyacrylamide gel electrophoresis.

A fifth aspect of the invention relates to an immunogenic composition which includes: (a) a substantially purified *C. parvum* antigen specifically recognizable by monoclonal antibody 3E2; and (b) a pharmaceutically acceptable carrier. In one embodiment, the *C. parvum* antigen is a glycoprotein with a molecular weight of approximately 1,400 KDa. In another embodiment, the carrier of the immunogenic composition can include an adjuvant.

A sixth aspect of the invention relates to a method of neutralizing *C. parvum* infection in a mammal, where the method includes the step of administering to the mammal a composition which includes an antibody having binding specificity for an epitope specifically recognizable by mAb 3E2. The administered composition can include monoclonal antibody 3E2 itself, and may include a *C. parvum* neutralizing amount of monoclonal antibody 3E2. Alternatively, the administered composition can include at least one monoclonal antibody other than monoclonal antibody 3E2. The administered composition can be administered orally.

Still another aspect of the invention relates to a method of stimulating an anti-*C. parvum* immune response in an animal. Practice of the invented method involves first obtaining an immunogenic composition that includes a purified *C. parvum* antigen dispersed in a pharmaceutically acceptable carrier, where the antigen is specifically recognizable by mAb 3E2, and then administering the composition to the animal according to a vaccination protocol. The immunogenic composition used in the invented method optionally can include an adjuvant.

DETAILED DESCRIPTION OF THE PREFERRED EMBODIMENT

As disclosed herein, the 3E2 monoclonal antibody (mAb) has binding-specificity for a *C. parvum* surface and apical glycoprotein complex of sporozoites and merozoites, and efficiently neutralizes *C. parvum* infection in vivo. Interestingly, the epitope recognized by the mAb 3E2 exhibits properties consistent with a carbohydrate/carbohydrate-dependent structure. More particularly, the target epitope, immobilized in a Western blotting format, was sensitive to degradation by glycosidase and degradation by periodate treatment, but resistant to protease digestion in a dot-blotting format. Thus, it is highly unlikely that the epitope could be expressed in recombinant form in a procaryotic host, for example. As will be apparent from the following disclosure, the production and isolation of the 3E2 hybridoma was made possible by the use of purified native *C. parvum* antigens as immunogens.

The present invention is useful for treating and preventing cryptosporidiosis in all mammals, including human neonates, and also in immunodeficient and certain immunocompetent children and adults. More particularly, the invented composition comprising the mAb 3E2 can be administered to young ruminants, for example, calves, goats and sheep. The invention is useful in these applications because young domestic ruminants serving as food animals are typically housed under conditions where exposure to *C. parvum* is unavoidable and typically do not possess functionally mature immune systems capable of fighting off infection at the time of exposure to the parasite. Another application of the invention relates to the control of cryptosporidiosis in humans having acquired or congenital immunodeficiencies, including individuals having acquired immunodeficiency syndrome (AIDS) resulting from infection with the human immunodeficiency virus (HIV).

Therapeutic or prophylactic compositions falling within the scope of the invention include preparations containing the mAb 3E2, optionally containing stabilizing agents including protease inhibitors, carrier proteins and pH buffering agents. A convenient source of agents known to stabilize antibodies, particularly when administered by oral route, is colostrum. Colostrum naturally contains antibodies which can, for example, be passed to a neonate. Thus, contemplated formulations for delivery of mAb 3E2 may involve dispersion of the mAb into colostrum prior to administration to a recipient mammal. Notably, experimental results presented herein proved that ascites preparations could be administered orally with strong retention of *C. parvum* neutralizing activity characteristic of mAb 3E2. This confirmed the utility of mAb 3E2 as an agent having powerful neutralizing activity directed against the parasite, *C. parvum*.

As disclosed herein, we have employed competition binding assays to identify mAbs having binding specificities for the same, similar or overlapping epitopes. Results of testing using these assays revealed that mAbs which neutralize *C. parvum* infection in vivo and which elicit the CSP-like reaction upon contacting sporozoites all have binding specificities that overlap the binding specificity of mAb 3E2. In view of the identity between neutralizing mAbs having the ability to elicit the CSP-like reaction and those having the ability to compete with mAb 3E2 for antigen binding, we concluded that identification of mAbs that compete with mAb 3E2 for antigen binding represents a method of identifying mAbs that can stimulate the CSP-like reaction in *C. parvum*. Moreover, our results support that any mAb that specifically competes with mAb 3E2 for antigen binding will also have neutralizing activity and be capable of stimulating the CSP-like reaction.

Another aspect of the invention relates to a method of stimulating an anti-*C. parvum* immune response in an animal using as an immunogen a purified glycoprotein constituent of C. parvum, wherein the constituent is characterized as a target for binding by mAb 3E2. Immunization with characterized molecules known to be the antigenic targets of a neutralizing humoral immune response, advantageously focuses the immune response against critical epitopes rather than against potentially irrelevant epitopes otherwise found in whole organism preparations. As described below, we have now defined critical epitopes disposed on the surface of C. parvum to which an antibody response must be directed in order to optimize immunoprotection against infection by this organism.

The hybridoma cell line secreting mAb 3E2-A8-B2 (3E2) has been deposited on Mar. 28, 1996 with the American Type Culture Collection, Manassas, Va., in compliance with the procedures specified for the deposit of biological materials under the Budapest Treaty. The deposit has been assigned accession number ATCC HB 12075.

The starting point for the development of the invention involved the purification of particular native antigens from C. parvum sporozoites. The C. parvum isolate used in the procedures described herein was obtained from H. Moon (National Animal Disease Center, Ames, Iowa). The C4A1 mAb, described in detail by Mead et al. (J. Parasit. 74:135 (1988)) and Arrowood et al. (Infect. Immun. 57:2283 (1989)), was used in the following procedure as an immunoaffinity purification reagent. Significantly, the purification protocol described below advantageously allowed the isolation of C. parvum protein constituents having posttranslational modifications that would have been absent from, for example, recombinant antigens produced in a heterologous host. General methods useful in immunoaffinity purification procedures can be found in Monoclonal Antibodies: Principles and Practice, 2nd ed. J. W. Goding, Academic Press, London (1986) pp. 219–227, the disclosure of which is hereby incorporated by reference.

Example 1 describes one procedure useful for isolating antigen constituents of C. parvum.

EXAMPLE 1

Isolation of C. parvum Antigens

The C4A1 mAb was purified from ascites fluid by an initial mixed mode resin cation exchange and affinity chromatography step and subsequently purified by HPLC to give an antibody preparation that was 96% pure IgM. These standard procedures were performed by the commercial laboratory service, TSD Bioservices (New York). Purified C4A1 was coupled to cyanogen bromide-activated sepharose 4B (Pharmacia Inc., Piscataway, N.J.) according to manufacturer's instructions. The derivatized matrix was then loaded into a column and optimal binding and elution conditions useful for isolating immobilized antigen were determined. Preparative level purification experiments were performed using C. parvum sporozoites that had been solubilized in lysis buffer consisting of 50 mM Tris HCl, 5 mM EDTA, 5 mM iodoacetamide, 0.1 mM N-a-p-tosyl-L-lysyl chloromethyl ketone (TLCK), 1 mM phenylmethanesulfonyl fluoride (PMSF) and 1% (wt/vol) octyl glucoside. Solubilized material was bound to the C4A1-coupled matrix, washed extensively and immobilized material eluted with 0.1 M glycine (pH 3.3).

Samples representing solubilized oocysts, solubilized sporozoites and immunoaffinity purified material were separated on a 10–20% polyacrylamide gel under reducing and denaturing conditions and the protein bands visualized by silver staining. The stained gel showed complex banding patterns representing more than approximately 100–150 protein species in the size range extending from approximately 21.5 kDa to greater than 200 kDa in the lanes corresponding to the crude solubilized preparations. In contrast, the lane representing immunoaffinity purified material gave a simpler pattern consisting of approximately 17 distinct protein bands. The stained bands were concentrated in the 25 to approximately 230 kDa size range. These results confirmed that the immunoaffinity purification procedure described above was useful for purifying native sporozoite constituents.

Western blotting using the C4A1 mAb as a probe was performed essentially according to the method described by Riggs et al. in Infect. Immun. 62:1927 (1994). In this procedure, samples of solubilized C. parvum sporozoites and immunoaffinity purified material were electrophoretically separated and Western blotted in parallel. Affinity-purified alkaline phosphatase conjugated goat anti-mouse IgM was used to detect binding of the C4A1 mAb following substrate addition. Results of the procedure indicated a correspondence between bands observed by SDS-PAGE and silver staining and immunoreactive proteins detectable by C4A1 staining in Western blots. Further, immunoreactive bands in immunoaffinity purified antigens comigrated with bands of similar molecular weight derived from whole organisms. This strongly suggested that the antigenic target of the C4A1 mAb was not a single species, but a small number of antigens that shared the same epitope. As a result of this size heterogeneity, the antigen recognized by the C4A1 mAb has been referred to as the "GP25-200" complex.

The immunoaffinity purified GP25-200 complex isolated according to the method described above was subsequently used as an immunogen in a step toward producing an expanded panel of hybridomas. General methods useful in the production of mAbs can be found in Monoclonal Antibodies: Principles and Practice, 2nd ed. J. W. Goding, Academic Press, London (1986) pp. 59–93, the disclosure of which is hereby incorporated by reference.

Example 2 describes the procedures used for immunizing mice with the immunoaffinity purified GP25-200 complex and producing antibody-secreting hybridomas.

EXAMPLE 2

Immunization of Mice with Purified GP25-200 Antigen and Preparation of Hybridomas Adult female BALB/c mice (Harlan Sprague Dawley, Indianapolis, Ind.) were immunized with 2 μg of immunoaffinity purified GP25-200 antigen incorporated in monophosphoryl lipid A trehalose dimycolate adjuvant (R-700, Ribi, Hamilton, Mont.) by intraperitoneal (i.p.) and subcutaneous (s.c.) administration. A second injection of 1 μg GP25-200 in adjuvant was given 7 weeks later by the same routes. Four weeks later, a third injection of 1 μg GP25-200 in adjuvant was given s.c. A final intravenous (i.v.) injection of 1.5 μg GP25-200 in phosphate buffered saline was given 5 weeks later. Three days following i.v. injection, spleens were removed and single cell suspensions prepared for fusion with SP2/0 myeloma cells. Cell fusions using SP2/0 myeloma cells and cloning by limiting dilution were performed as described by McGuire et al. in Am. J. Vet. Res. 44:1284 (1983).

Preliminary indirect immunofluorescence assays using heat-fixed sporozoites as antigenic targets were used to identify hybridomas having specificity for GP25-200. Results from this preliminary screening indicated that 112 of the hybridomas were positive for sporozoite binding. These hybridomas were found to have heterogeneous indirect immunofluorescence patterns that included apical reactivity, surface membrane reactivity in a multifocal or diffuse pattern and/or multifocal internal binding.

Hybridoma supernatants that gave positive staining results in the preliminary assay were then screened for surface-reactive anti-GP25-200 antibody by the live indirect immunofluorescence assays described by Riggs et al. in *Infect. Immun.* 55:2081 (1987) and Mishell et al. in *Selected Methods in Cellular Immunology*, B. B. Mishell and S. M. Shiigi, eds. W. H. Freeman and Company, San Franscisco, Calif. p.19 (1980). The disclosures of these two citations are hereby incorporated by reference. Fluorescein-conjugated goat anti-mouse Ig (IgA, IgG, IgM) second antibody (Cooper Biomedical, Malvern, Pa.) was used to detect binding of anti-GP25-200 antibody. mAb isotypes and concentrations were determined by immunodiffusion according to the method of Johnstone et al. in *Immunochemistry in Practice*, A. Johnstone and R. Thorpe, eds. Blackwell Scientific Publications, Boston, p. 120 (1982).

Example 3 describes the method used to screen hybridoma supernatants to identify mAbs specific for the GP25-200 antigen.

EXAMPLE 3

Indirect Immunofluorescence Assay to Identify mAbs Specific for GP25-200

Hybridoma culture supernatants were screened for surface-reactive anti-GP25-200 antibody by live indirect immunofluorescence according to the method described by Riggs et al. in *Infect. Immun.* 55:2081 (1987) and Mishell et al. in *Selected Methods in Cellular Immunology*, B. B. Mishell and S. M. Shiigi, eds. W. H. Freeman and Company, San Franscisco, Calif. p.19 (1980), the disclosures of which are hereby incorporated by reference. All steps were performed at 4° C. by using viable sporozoites ($5\times10^7$/ml) in PBS with 0.5% (wt/vol) bovine serum albumin (PBS–BSA; Sigma Chemical Co., St Louis, Mo.). The assay was performed in 96-well V-bottom microtiter plates (Flow Laboratories). All dilutions were made with PBS–BSA. A total of 50 μl of hybridoma supernatant and 50 μl of sporozoite preparation per well were incubated for 30 minutes and then washed four times with 200 μl of PBS–BSA per well (3,500×g). A total of 50 μl of fluorescein-conjugated goat anti-mouse Ig (IgA, IgG, IgM) second antibody (Cooper Biomedical, Malvern, Pa.) was used to detect binding of anti-GP25-200 antibody. mAb isotypes and concentrations were determined by immunodiffusion according to the method of Johnstone et al. in *Immunochemistry in Practice*, A. Johnstone and R. Thorpe, eds. Blackwell Scientific Publications, Boston, p. 120 (1982).

Results indicated that five of the mAbs tested in the live indirect immunofluorescence assay were found to give a posteriorly capped staining pattern on sporozoites with posteriorly extruded fluorescent material, suggesting the presence of shed antigens. Further, clumped collections of fluorescent material free of intact sporozoites were also observed. This indicated that the antigen targets of the five referenced mAbs were being shed in a manner reminiscent of the CSP reaction previously reported for malaria (Cochrane et al. *J. Immunol.* 116:859 (1976); Nussenzweig et al. *Cell* 42:401 (1985)). Additionally, these mAbs were found to bind to oocyst walls. One of the five mAbs, an IgM (kappa light chain) called 3E2, was subsequently examined more closely in functional assays.

In view of the binding properties of the anti-GP25-200 mAbs disclosed above, it was of interest to determine whether any of the mAbs also possessed the ability to neutralize *C. parvum* infection. Two different types of neutralizing assays were employed to make this determination. In the first assay, mAbs and sporozoites were combined and incubated prior to intraintestinal injection into young mice. In the second assay, neonatal mice were orally coadministered with mAb and *C. parvum* oocysts. Significantly, a positive result in the second assay, wherein the mAb exhibits neutralizing activity, additionally confirms that the mAb retains antigen binding activity under gastrointestinal conditions. The following Example describes a generalized procedure and presents results obtained using the mAb 3E2.

Example 4 describes the first of two methods used for identifying mAbs that can neutralize *C. parvum* infection.

EXAMPLE 4

Sporozoite Neutralization Assay

Assays were performed in 96-well round-bottom tissue culture plates (Flow Laboratories). The isolated sporozoite suspension (15 μl) in MEM was added to each well, mixed with an equal volume of mAb, incubated at 37° C. for 30 minutes in a 5% $CO_2$ atmosphere. Following incubation, sporozoites were suspended by drawing up and then gently expulsing the well contents 5 times with a 25 μl syringe (Hamilton Co., Reno, Nev.). A total of 25 μl from each well containing $2\times10^5$ sporozoites was then injected intraintestinally into 7-day-old specific-pathogen-free BALB/c mice. Uninfected control mice received 25 μl of MEM. Groups of mice were injected with sporozoites that had been incubated with isotype control mAb or 3E2. A 25 μl syringe fitted with a 4 cm length of polyethylene tubing (outer diameter, 0.61 mm; Clay Adams Co., Parsippany, N.J.) was used for intraintestinal injection. The tubing was inserted 2 cm into the colon through the anus prior to injection. Following injection, mice were maintained in a 37° C. incubator. Removable rubber patches were used to prevent defecation for 5 hours postinjection before mice were returned to their dams. Each group of mice was caged separately in containers fitted with filter tops.

Mice were euthanized with ether 96 hours postchallenge. The entire intestinal tract was collected immediately after euthanasia, cut into 2.5 cm sections, and fixed longitudinally in buffered Formalin. Hematoxylin-eosin stained longitudinal sections representing the entire length of the intestinal tract from each mouse were prepared, assigned randomly selected numerical codes, and examined histologically without knowledge of treatment, and infection scores were determined. Scores of 0, 1, 2, or 3 representing the density of organisms per unit length of intestinal mucosa were assigned for terminal jejunum and ileum, cecum and colon (0, absence of infection; 1, 1–33% of mucosa parasitized; 2, 34–66% of mucosa parasitized; 3, greater than 67% of mucosa parasitized). Cumulative scores ranged from 0 (no infection) to 9 (maximum infection) for individual mice. Results of the scoring are presented in Table 1.

TABLE 1

Neutralization of *C. parvum* Sporozoite Infectivity by mAb 3E2

| Inoculum | No. Infected/ No. Inoculated | Mean Infection Score ± SD | P |
|---|---|---|---|
| Sp + 3E2 | 0/10 | 0 | <0.0001 |
| Sp + Control IgM | 10/10 | 4.4 ± 1.2 | |

The results in Table 1 indicated that mAb 3E2 had *C. parvum* neutralizing activity when the mAb was first combined with sporozoites ex vivo and then administered intraintestinally. However, a more stringent test of the applicability of the neutralizing activity of this mAb preparation involved coadministration of oocysts and ascites by the oral route. This test is believed to more closely reflect the efficacy of the mAb as it is used as a therapeutic or prophylactic agent. A description of this more stringent test follows.

Example 5 describes the method used to demonstrate that the mAb 3E2 could be administered orally to laboratory animals and retain C. parvum neutralizing activity.

EXAMPLE 5

Neutralizing Activity of mAb 3E2 in vivo

Neonatal BALB/c mice develop intestinal infections following oral administration of $10^4$ peracetic acid-treated C. parvum oocysts (Riggs et al. Infect. Immun. 62:1927 (1994); Riggs et al. Infect. Immun. 55:2081 (1987); Perryman et al. Molec. Biochem. Parasitol. 80:137 (1996)). The ability of mAb 3E2 to diminish infection was tested by orally administering 100 μl of ascites containing the mAb at the time of, as well as at 2 and every 12 hours thereafter following oral challenge with $10^4$ oocysts. Mice were terminated 92 to 94 hours following oocyst administration. Intestinal tracts were removed and scored histologically for the presence and number of C. parvum organisms in epithelial cells of the removed jejunum and ileum, cecum and colon. Control mice received isotype control mAb of irrelevant specificity. Scores of 0–3 were assigned for each of the three sites, with 0 indicating no organisms; 1,<33% parasitized; 2, 33–66% of cells parasitized; and 3,>than 66% of cells parasitized. Scores from the three sites were summed to obtain an infection score for each mouse. Score differences between groups of mice were analyzed by Student's t test. Results of the scoring are presented in Table 2.

TABLE 2

Protection Against Challenge with C. parvum Oocysts by mAb 3E2

| Expt. and Inoculum | No. Infected/ No. Inoculated | Mean Infection Score ± SD | P |
|---|---|---|---|
| Expt 1 mAb 3E2 | 4/6 | 0.7 ± 0.5 | <0.0001 |
| Control IgM | 8/8 | 4.5 ± 1.5 | |
| Expt 2 mAb 3E2 | 4/7 | 0.9 ± 0.9 | <0.0001 |
| Control IgM | 8/8 | 5.1 ± 1.5 | |

The results in Table 2 demonstrated that orally administered neutralizing mAb can mediate significant neutralization of C. parvum infection in vivo.

While mAb 3E2 showed particularly strong neutralizing activity in the in vivo assay described above, we discovered that other mAbs specific for C. parvum constituents also could confer significant protection in vivo. The following Example discloses that a collection of mAbs generated against various purified constituents of C. parvum were tested for neutralizing activity in vivo along with one of the samples disclosed in Table 2. The results of the in vivo assay confirmed that neutralizing mAbs can survive gastrointestinal transit and mediate neutralization during the short time that zoites are extracellular.

Example 6 describes the methods used to demonstrate that a broad spectrum of C. parvum neutralizing mAbs retained activity in vivo.

EXAMPLE 6

Production and Characterization of a mAb Panel Having C. parvum Neutralizing Activity In Vivo Native antigens corresponding to CPS-500 and GP-23 were isolated and used according to the methods of Examples 1–3 to prepare and identify hybridomas secreting anti-C. parvum mAbs. mAb C6B6 was immobilized to a solid matrix to produce an immunoaffinity column that was used to purify GP-23. Notably, the CPS-500 antigen was non-protein in composition. The CPS-500 antigen was isolated by silicic acid chromatography according to standard methods. The mAbs secreted by the hybridomas, together with a collection of mAbs generated against the GP25-200 antigen complex in Examples 1–3, including mAb 3E2, were tested in the in vivo neutralizing assay disclosed in Example 5. Results of the neutralizing assay are presented in Table 3.

TABLE 3

Immunotherapeutic Effect of Neutralizing mAbs Against Intestinal Cryptosporidiosis

| | | | Mean Infection Score + SD | | |
|---|---|---|---|---|---|
| mAbs | Prepared Against | Isotype | Test mAbs | Control mAbs | P |
| 3H2/1B5 | GP25-200/GP25-200 | -/IgM | 2.5 ± 2.0 | 6.3 ± 1.3 | <0.005 |
| 3E2/4G7 | GP25-200/GP25-200 | IgM/IgM | 1.9 ± 2.0 | 6.3 ± 1.3 | <0.0001 |
| 4C11/3A12 | GP23/GP25-200 | IgM/IgM | 3.6 ± 0.8 | 5.7 ± 1.5 | <0.005 |
| 7D10/3D6 | GP23/GP25-200 | $IgG_1$/IgM | 2.6 ± 1.4 | 5.9 ± 1.6 | <0.001 |
| 1E10/3E1 | GP23/GP25-200 | $IgG_1$/IgM | 3.6 ± 0.5 | 5.9 ± 1.6 | <0.005 |
| 3A10/3D10 | GP25-200/GP25-200 | IgM/IgM | 3.0 ± 0.9 | 5.7 ± 1.5 | <0.005 |
| 3B12/3D1 | GP25-200/GP23 | IgM/IgM | 1.1 ± 1.6 | 4.8 ± 1.8 | <0.001 |
| 7G9/3C8 | GP23/GP25-200 | $IgG_{2a}$/IgM | 2.4 ± 1.6 | 4.5 ± 1.6 | <0.01 |
| 4E11/3B5 | GP25-200/GP25-200 | $IgG_1$/IgM | 2.1 ± 1.1 | 5.3 ± 1.1 | <0.0001 |
| 4H5/7C2 | GP25-200/GP23 | IgM/$IgG_{2a}$ | 0.6 ± 1.0 | 5.2 ± 1.1 | <0.0001 |
| 3G1/2F5 | GP25-200/GP25-200 | IgM/IgM | 5.3 ± 1.5 | 7.0 ± 0.7 | <0.05 |
| 3E6/4E4 | GP25-200/GP25-200 | $IgG_1$/$IgG_3$ | 1.8 ± 1.5 | 5.1 ± 1.6 | <0.0005 |
| 1A9/1F5 | GP23/GP25-200 | $IgG_3$/IgM | 3.8 ± 1.4 | 5.1 ± 1.6 | <0.05 |
| 7H12 | GP23 | $IgG_1$ | 5.2 ± 1.1 | 6.9 ± 0.7 | <0.005 |
| 4B10 | GP25-200 | IgM | 3.8 ± 1.4 | 5.2 ± 1.1 | <0.01 |
| 3E2 | GP25-200 | IgM | 0.7 ± 0.5 | 4.5 ± 1.5 | <0.0001 |

The quantitative results presented in Table 3 indicated that several of the mAbs raised against purified C. parvum constituents possessed neutralizing activity that was retained following oral administration. These results additionally confirmed that mAb 3E2 possessed superior neutralizing activity when compared with other mAbs tested in the procedure described above.

Pools of anti-C. parvum mAbs, including mAb 3E2, optimized for neutralizing activity represent particularly advantageous therapeutic compositions useful in the practice of the invention. Whereas antigenic drift could conceivably lead to the loss of an epitope recognized by a single anti-C. parvum mAb, and corresponding loss of neutralizing activity of a mAb targeted to that epitope, it is highly unlikely that antigenic drift would lead to the simultaneous loss of several different epitopes recognized by a collection of anti-C. parvum mAbs. Accordingly, therapeutic compositions comprising the particularly advantageous mAb 3E2 in combination with other mAbs having binding specificities for other C. parvum neutralizing epitopes represent particularly useful compositions for providing passive immunity to C. parvum infection.

In view of the particularly advantageous properties of mAb 3E2, an experiment was conducted to confirm that a composition comprising mAb 3E2 in combination with other anti-C. parvum mAbs exhibited strong neutralizing activity in vivo. A pool of three mAbs of irrelevant binding specificity and having the $IgG_1$, IgM and $IgG_3$ isotypes served as a negative control in the procedure. Thus, neutralizing activity detected in the experimental trial was attributable to the specificity of anti-C. parvum mAbs in the pool. The pool of anti-C. parvum mAbs tested in the procedure described below included mAbs 18.44, C6B6, C4A1, 2B4, 3D1, 3E2 and M23A1. The results described in the following Example clearly indicated that a composition comprising mAb 3E2 and other anti-C. parvum mAbs exhibited strong neutralizing activity in vivo.

Example 7 describes the method used to demonstrate that a cocktail of anti-C. parvum mAbs exhibited strong neutralizing activity in vivo.

EXAMPLE 7

Additive Therapeutic Effect of mAb Pools Targeting Multiple Neutralization-Sensitive C. parvum Epitopes Hybridomas secreting mAbs listed in the first column of Table 4 were separately propagated in BALB/c mice and ascites fluid samples containing the mAbs collected using standard laboratory methods. These mAb preparations were administered to neonatal BALB/c mice as pools of ascites fluid to test the in vivo neutralizing capacity of the preparations according to the method described under Example 5. The volume of ascites fluid administered to neonatal mice in this procedure was held constant at 150 μl. Equal volumes of different ascites fluid samples were mixed to create preparations of mAb combinations. A pool or collection of mAbs HL113 (IgM), HL245 ($IgG_3$) and HL296 ($IgG_1$), all having irrelevant binding specificities, served as a negative control in the procedure. A second pool included mAbs 18.44, C6B6, C4A1, 2B4, 3D1, 3E2 and M23A1, all having binding specificities for epitopes disposed on C. parvum. In this procedure, 8–10 mice were used for each test group.

The results of the procedure testing the neutralizing activity of pooled mAbs are presented in Table 4. Plus and minus signs in the Table indicate the antigens against which mAbs in the pools were generated. The negative control mAbs HL113, HL245 and HL296 were not prepared against any of CPS-500, GP-23 or GP25-200, and do not bind to C. parvum. The mAbs 18.44 and 2B4 had binding specificities directed against CPS-500; mAbs C6B6 and 3D1 had binding specificities directed against GP-23; while mAbs C4A1 and 3E2 had binding specificities directed against GP-25-200. The mAb M23A1 was prepared against the merozoite stage (MZ in the Table).

TABLE 4

Therapeutic Effect of mAb Pools Targeting Multiple Neutralization-Sensitive C. Parvum Epitopes

| mAb Pool | PREPARED AGAINST | | | | Mean Infection Score ± SD |
|---|---|---|---|---|---|
| | CPS-500 | GP-23 | GP25-200 | $MZ^c$ | |
| HL113/HL245/ HL296 (isotype controls) | − | − | − | − | 4.8 ± 0.4 |
| 18.44/2B4 | +/+ | | | | |
| C6B6/3D1 | | +/+ | | | |
| C4A1/3E2 | | | +/+ | | |
| M23A1 | | | | + | $1.4 ± 1.0^{a,b}$ |

$^a$P < 0.0001 compared to control
$^b$P < 0.0001 compared to 18.44/C6B6/C4A1 (3 mAbs originally used to define CPS-500, P23 and GP25-200, respectively)
$^c$merozoite stage The results presented in Table 4 demonstrated that a pool or collection of anti-C. parvum mAbs that included mAb 3E2 was useful as a therapeutic composition having C. parvum neutralizing activity. More specifically, the mean infection score of 4.8±0.4 obtained in the negative control trial represented a baseline for infectious activity. The mean infection score was dramatically reduced to a value of 1.4±1.0 in mice receiving a composition comprising mAb 3E2 in combination with other C. parvum neutralizing mAbs. Thus, in this experiment the mean infection score measured in animals receiving a pool of mAbs that included mAb 3E2 was approximately 30% of the score measured in animals receiving pooled negative control mAbs. While this level of reduction was significant, it was not as dramatically reduced as it was in animals that received mAb 3E2 in the experiment presented in Table 2 and 3. More particularly, the group of animals that received mAb 3E2 alone showed mean infection scores representing only about 15% of the negative control value. In aggregate, these results indicated that mAb 3E2 alone exhibited unexpectedly strong C. parvum neutralizing activity and that compositions including mAb 3E2 in combination with other mAbs directed to different neutralizing epitopes also exhibited strong neutralizing activity.

Example 8 describes the method used to demonstrate that mAb 3E2 had binding specificity for a carbohydrate/carbohydrate-dependent structure.

EXAMPLE 8

The Antigenic Target of mAb 3E2 Comprises a Carbohydrate

The method described by Woodward et al. in J. Immunol. Methods 78:143 (1985) was modified by using 2–12% SDS-PAGE as well as 10–20% SDS-PAGE separations to examine the chemical identity of the epitope recognized by mAb 3E2. More specifically, Western blotted protein samples from solubilized sporozoites were either left as untreated controls or treated with 5 mM periodate prior to detection with the mAb 3E2.

Results of these procedures indicated that mAb 3E2 had binding specificity for a carbohydrate/carbohydrate-dependent moiety disposed on a glycoprotein. The untreated control lanes of the blot that had been probed with 3E2 revealed multiple bands having molecular weights of approximately 46, 51, 70, 84, 106, 112, 117, 120, 134, 147, 154, 158, 172, 183, 220, 230, 265, and a diffuse band in the size range of 1200–1400 kDa. However, no staining pattern was detected in the sample lane that received periodate treatment. This indicated that the epitope recognized by the mAb probe was destroyed by periodate oxidation and had a carbohydrate/carbohydrate dependent structure. The observations that the target of mAb 3E2 binding was periodate sensitive; could be visualized on Western blots and could be stained by protein-detecting reagents (Example 1) all indicated that 3E2 had binding specificity for a carbohydrate/carbohydrate-dependent structure disposed on a glycoprotein molecule.

As indicated above, the neutralizing mAb 3E2 will find important application in the control and prevention of cryptosporidiosis in humans, including patients infected with HIV (AIDS). Routes of administration for pharmaceutical compositions that include mAb 3E2 include oral and intraintestinal administration according to methods that will be apparent to those having ordinary skill in the art. Alternative methods of delivery of the therapeutic mAb 3E2 preparation include: lyophilized preparations; alternative carrier systems including dispersion into colostrum; encapsulation; and time-release encapsulation for oral administration and post gastric release. Effective dosages may be empirically determined, but will ordinarily be sufficiently high that oocyst levels detectable in fecal samples will decrease substantially within a few days following the first administration of the mAb 3E2 containing composition. Finally, there are no known adverse side effects known to accompany administration of the mAb 3E2 composition and it is believed that individuals may be administered with the composition until diarrhea symptoms dissipate or indefinitely.

Example 9 describes how a preparation including the mAb 3E2 can be administered to a human patient infected by C. parvum.

EXAMPLE 9

Method of Providing Passive Immunity to Infection by C. parvum

An AIDS patient experiencing diarrhea as the result of infection with C. parvum is first identified. A baseline measurement indicates the presence of high numbers of oocysts present in a fecal sample.

The patient is administered with a buffered preparation containing bovine colostrum and mAb 3E2 in an amount of up to 1 g of the mAb. The mAb has been produced in a bioreactor under serum-free conditions and is not associated with infectious agents. The colostrum serves as a carrier for the mAb and provides a source of stabilizing agents that preserve the neutralizing activity of the mAb. The patient is administered with the preparation twice daily.

The patient's clinical parameters show improvement within a few days following administration of the mAb-containing preparation. The patient's diarrhea dissipates and the oocyst quantitation in a fecal sample is decreased to a very low level. These results confirm that oral administration of a preparation including the mAb 3E2 is of therapeutic value.

Although the foregoing Example provides a description of a therapeutic application of the mAb 3E2, prophylactic applications wherein an individual receives the mAb prior to C. parvum exposure can also be carried out.

Experimental results presented above indicated that mAb 3E2 was one of five mabs directed against the GP25-200 and high molecular weight glycoprotein that stimulated the CSP-like reaction in sporozoites when tested in a live indirect immunofluorescence assay. This CSP-like reaction was characterized by progressive extrusion and eventual shedding of membranous material from the sporozoite posterior and resembled the CSP reaction described for malarial sporozoites by Cochrane et al. in J. Immunol. 116:859 (1976). Progressive rounding of C. parvum sporozoites after contacting mAb 3E2 suggested osmoregulatory dysfunction or perhaps premature triggering to the trophozoite stage. The CSP-like reaction was initiated at the apical end of C. parvum sporozoites and posterior translocation of the antigen was inhibitable by treatment of sporozoites with 5 $\mu$M cytochalasin-D. This latter observation indicated that the reaction was dependent on an intact cytoskeletal apparatus and microfilaments.

Significantly, we have also determined that the merozoite stage of C. parvum undergoes the CSP-like reaction upon contacting mAb 3E2. The CSP-like reaction observed in the merozoite was morphologically indistinguishable from that which occurred in the sporozoite stage. All mAbs which elicited the CSP-like reaction did so within seconds of contacting sporozoites or merozoites in vtro and provided near complete protection against infectivity in vivo.

Interestingly, the epitope recognized by mAb 3E2 was localized to sporozoite apical complex organelles, including electron-dense granules. More particularly, immunoelectron microscopy performed using either mAb 3E2 or an isotype-matched control IgM mAb and sporozoites showed that electron-dense granules were predominantly labeled by mAb 3E2.

Example 10 describes the method used to localize the antigen bearing the epitope recognized by mAb 3E2 prior to and during the CSP-like reactions.

EXAMPLE 10

Localization of the Epitope Recognized by mAb 3E2

Sporozoites were purified by anion exchange chromatography according to the method described by Riggs et al. in Infect. Immun. 55:2081 (1987), and either fixed immediately for immunoelectron microscopy in a solution of 2% [v/v] paraformaldehyde and 0.5% [v/v] glutaraldehyde in HBSS for a period of 15 minutes, or first incubated with mAb 3E2 or isotype-matched control mAb, allowed to undergo the CSP-like reaction and then washed and fixed. Samples were washed twice in HBSS, dehydrated with 95% ethanol and embedded in LR white resin. Sections were mounted on nickel grids and blocked with PBS made with 0.1% (w/v) BSA and 0.1% (v/v) TWEEN 20 for 10 minutes at 21° C. Sporozoites that had been fixed and embedded without exposure to mAb 3E2 while viable were incubated overnight at 4° C. on drops of mAb 3E2 or isotype-matched control, washed four times with PBS, and incubated with affinity-purified rabbit anti-mouse IgM (Zymed, San Francisco, Calif.), washed again, and incubated with affinity-purified colloidal gold conjugated goat anti-rabbit IgG (Zymed, 20 nm or 5 nm, EM grade). Finally, grids were washed and post-fixed with an aqueous solution of 4% (w/v)

formaldehyde, 1% (v/v) glutaraldehyde for studies localizing the antigenic target of mAb 3E2. Sporozoites which had been exposed to 3E2 prior to fixation and embedding were blocked and incubated with rabbit anti-mouse IgM and colloidal gold antibodies as above to provide a means of visualizing the CSP-like reaction. Immunostained samples were observed and photographed with a JEOL 100 CX EM at 80 KV.

Results indicated dense mAb 3E2 immunogold labelling of apical organelles, including electron-dense granules. Identification of labelled organelles as apical complex, including dense granules was confirmed by comparison with the published ultrastructural morphology presented by Current et al. in *J. Protozool* 33:98 (1986) and Fayer et al. in J P Dubey, C A Speer and R Fayer (eds.), *Cryptosporidiosis of Man and Animals*, CRC Press, Ch 1 (1990).

In view of the desirable properties of mAb 3E2 and the other four mAbs that similarly stimulated the CSP-like reaction in *C. parvum*, it was of interest to better assess the properties that were shared by these mAbs. Although not explicitly shown below, our finding that mAbs 3E2, 3B12, 3A12, 3A11 and 3E6 all gave identical patterns on Western blots and by indirect immunofluorescence suggested that the mAbs recognized the same antigen.

As disclosed in the following Example, all five mAbs having the ability to stimulate the CSP-like reaction bound an epitope that was identical to, or closely related to, the epitope bound by mAb 3E2. More specifically, the results disclosed in the following two Examples demonstrated that mAbs which stimulated the CSP-like reaction also competed with mAb 3E2 for antigen binding. Accordingly, we discovered that the ability to compete with mAb 3E2 for binding to the GP25-200 and 1,200–1,400 KDa antigen target represented a useful criterion for identifying mAbs having the ability to stimulate the CSP-like reaction.

Example 11 describes one method used to demonstrate that mAbs having the ability to stimulate the CSP-like reaction also had binding specificities similar to that of mAb 3E2.

EXAMPLE 11

Competition ELISA Using Biotinylated mAb 3E2 and Peroxidase-Labelled Streptavidin for Detection Purified sporozoites dispersed in PBS containing protease inhibitors were disrupted by sonication and repetitive freeze-thaw cycles according to standard methods. The lysate was centrifuged at 16,000×g for 30 minutes (4° C.), and the supernatant isolated. The individual wells of 96 well plates were then coated with the equivalent of 5×10$^5$ solubilized sporozoites/well for a period of 12 hours (4° C.). The wells were washed, blocked with fish gelatin (3.5% w/v) and washed again, all according to standard laboratory methods. Wells in triplicate were then incubated for 1 hour either with unlabeled, individual: (1) mAbs 3E2, 3B12, 3E6, 3A12 or 3A11; (2) mAbs 1G2, 2D10, 7B6, C6B6 or C4A1, all of which recognized *C. parvum* epitopes distinct from the epitopes recognized by mAbs in the preceding group based on results obtained from Western blotting, and none of which elicited the CSP-like reaction; or (3) IgM isotype matched control mAb HL113 having an irrelevant binding specificity. All mAb reagents were added in volumes of 100 $\mu$l/well to a final concentration of 30 $\mu$g/ml of mAb. Following incubation for 1 hour, biotinylated mAb 3E2 was added in a volume of 25 $\mu$l/well to give a final mAb 3E2 concentration of 1 $\mu$g/ml. Samples were incubated an additional 30 minutes, washed, incubated 30 minutes with peroxidase-labelled streptavidin (100 $\mu$l/well of a 0.5 $\mu$g/ml solution), washed and exposed to ABTS peroxidase substrate according to the method described by the manufacturer (Kirkegaard and Perry). Absorbances at a 405 nm wavelength (OD$_{405}$) were read on an ELISA plate reader and are presented in Table 5. Notably, each data point presented in Table 5 represents the mean of five replicate wells.

TABLE 5

Competition ELISA Using Biotinylated mAb 3E2 and Peroxidase-Labeled Streptavidin for Detection

| mAb Type | Unlabeled mAb | OD$_{405}$ |
| --- | --- | --- |
| Control | HL113 | 0.91 |
|  | IG2 | 0.85 |
|  | 7B6 | 0.78 |
|  | C6B6 | 0.84 |
|  | C4A1 | 0.83 |
| CSP-Stimulatory | 3E2 | 0.10 |
|  | 3B12 | 0.15 |
|  | 3E6 | 0.09 |
|  | 3A12 | 0.15 |
|  | 3A11 | 0.10 |

The results presented in Table 5 indicated that all of the mAbs having the ability to stimulate the CSP-like reaction recognized the same, similar or overlapping epitopes as that recognized by mAb 3E2. More particularly, mAbs 3E2, 3B12, 3E6, 3A12 and 3A11 all reduced the amount of biotinylated mAb 3E2 that was immobilized in the wells of the ELISA plate as reflected by less significant production of the colored reaction product detectable at the 405 nm wavelength. Significantly, none of the control mAbs recognized the same epitope as that recognized by mAb 3E2 based on Western blotting results. Moreover, control mAbs HL113, IG2, 7B6, C6B6 and C4A1 showed no evidence for competition with mAb 3E2. The entry corresponding to the unlabeled mAb 3E2 in Table 5 represented a perfect competitor for the biotinylated mAb 3E2 while the negative control mAb HL113 represented no competition.

Example 12 describes a second method useful for demonstrating that mAbs capable of eliciting the CSP-like reaction in *C. parvum* also recognized the same, similar or overlapping epitope as that recognized by mAb 3E2. The results of this radioimmuno assay (RIA) procedure confirmed the findings presented in the preceding Example.

EXAMPLE 12

Competition RIA using $^{125}$I-Labelled mAb 3E2 for Detection

Immulon-4 removable wells were coated with the equivalent of 5×10$^5$ purified sporozoites/well exactly as described in the preceding Example. Wells, in replicates of five, were then washed, blocked with PBS–BSA (2% w/v), washed again, incubated for 3 hours (37° C.) with unlabeled, individual: (1) mAbs 3E2, 3B12, 3A12 or 3A11; or (2) mAbs C6B6, 7D10, 4D5, 1D8, 3A3, 1B5, IG1, 3A7 or 3H1. The mAbs in the second group all recognized *C. parvum* epitopes distinct from the epitopes recognized by the mAbs in the first group based on the results of Western blotting. None of the mAbs in the second group elicited the CSP-like reaction. All mAbs were added in a volume of 200 $\mu$l/well with a final concentration of 8 $\mu$g/ml of the mAb. Samples were incubated for 1 hour (37° C.) with $^{125}$I-labeled (Iodogen, Pierce) mAb 3E2 (50 $\mu$l/well, 2 $\mu$g/ml final concentration of mAb), washed, and counted in a gamma counter. Results representing the mean of five replicate wells are presented in Table 6.

TABLE 6

Competition RIA Using Radiolabeled mAb 3E2 for Detection

| mAb Type | Unlabeled mAb | Immobilized Radioactivity (CPM) |
|---|---|---|
| Control | C6B6 | 14,599 |
|  | 7D10 | 12,655 |
|  | 4D5 | 14,664 |
|  | 1D8 | 14,340 |
|  | 3A3 | 13,961 |
|  | 1B5 | 13,257 |
|  | IG2 | 15,581 |
|  | 3A7 | 13,341 |
|  | 3H1 | 15,061 |
| CSP-Stimulatory | 3E2 | 1,364 |
|  | 3B12 | 1,870 |
|  | 3A12 | 3,845 |
|  | 3A11 | 2,451 |

The results presented in Table 6 again indicated that mAbs which stimulated the CSP-like reaction also competed with mAb 3E2 for antigen binding. None of the unlabeled control mAbs in Table 6 showed evidence for competition with radiolabeled mAb 3E2 for epitope binding. All of the samples that included control mAbs gave levels of immobilized, radiolabeled mAb 3E2 substantially higher than the level observed when unlabeled mAb 3E2 was used as the competitor. Thus, mAb 3E2 served as a positive control for the competition while the control mAbs represented non-competing negative controls in the procedure. All of the mAbs having CSP-like reaction stimulatory activity led to reductions in the level of immobilized, radiolabeled mAb 3E2, thereby providing evidence for binding competition with radiolabeled mAb 3E2. These inhibition results indicated that mAbs 3E2, 3B12, 3A12 and 3A11 recognized the same, similar, or overlapping epitopes.

Thus, the results of the competition binding assays presented in the two preceding Examples confirmed an absolute correlation between mabs that competed with mAb 3E2 for antigen binding and mAbs that stimulated the CSP-like reaction. It follows that any mAb that has the ability to compete with mAb 3E2 for epitope-binding will also stimulate the CSP-like reaction. In view of these findings and conclusions, we reasoned that the antigenic target of mAb 3E2 played a critical role in the mechanism of the CSP-like reaction. Accordingly, we proceeded to identify and isolate the molecular species bound by mAb 3E2.

Example 13 describes the method used to demonstrate that membranous material shed by sporozoites after contacting mAb 3E2 was of high molecular weight and was highly glycosylated. Glycosylation status of the shed material was inferred from: (a) the carbohydrate nature of the target epitope, (b) highly variable migration of the material during SDS-PAGE typical of glycoproteins, and (c) a significant decrease in molecular weight following deglycosylation and separation by SDS-PAGE. Also disclosed is the discovery that the high molecular weight species mechanistically involved in the CSP-like reaction is an exoantigen constitutively released by infectious sporozoites.

EXAMPLE 13

PERCOLL Density Gradient Purification of Membranous Material Shed After the mAb 3E2-Induced CSP-Like Reaction mAb 3E2 (288 $\mu$g) was incubated with $5 \times 10^8$ excysted oocysts for a period of 1 hour (37° C.) until the CSP-like reaction, characterized by membranous precipitate formation on sporozoites, was maximal. A 1 ml sample of the preparation was layered onto 9.0 mls of a PERCOLL (Pharmacia, Piscataway, N.J.) solution consisting of 9 parts PERCOLL, 1 part 10x Alsever's solution (4.2 g NaCl/liter; 8.0 g trisodium citrate dihydrate/liter; 20.5 g glucose/liter) purchased from GIBCO-BRL (Grand Island, N.Y.), and 9 parts 1x Alsever's solution in a centrifuge tube. Membranous precipitates were recovered from the gradient following centrifugation at 40,000×g for 30 minutes (4° C.). Gradient fractions were removed sequentially and examined by phase contrast microscopy for the presence of membranous precipitates. The preparation separated into five zones. In order from lowest to highest density, these zones represented: (1) oocyst walls, (2) membranous precipitates, (3) precipitates attached to sporozoites, (4) sporozoites and (5) intact oocysts. Precipitate-containing fractions were washed four times by centrifugation at 16,000×g for 10 minutes (4° C.) using PBS containing protease inhibitors (5.0 mM EDTA, 5.0 mM iodoacetamide, 0.1 mM N-tosyl-L-lysl chloromethyl ketone, 1.0 mM phenylmethylsulfonyl fluoride) and then subjected to 6–8 sequential PERCOLL gradients until the precipitate fraction was relatively free of sporozoite, intact oocyst, and oocyst wall contamination. Purified membranous precipitates were pelleted at 16,000×g for 10 minutes (4° C.), resuspended in 0.03 ml lysis buffer (50 mM Tris, 5.0 mM EDTA, 5.0 mM iodoacetamide, 0.1 mM N-tosyl-L-lysl chloromethyl ketone, 1.0 mM phenylmethyl-sulfonyl fluoride, and 1% [wt/vol] n-octyl-B-D-glucopyranoside), solubilized for 30 minutes (4° C.) and stored at −80° C. until analysis.

A silver stained 2–12% gradient SDS-PAGE reducing gel demonstrated the presence of a single prominent, approximately 1400 kDa band (CSL) in membranous material shed from viable sporozoites during the CSP-like reaction. Lower molecular weight bands co-migrated with IgM mAb controls, indicating that CSL was the antigen species recognized by mAb 3E2 during the CSP-like reaction.

The results presented in the foregoing Example indicated that the mechanism of the mAb 3E2 stimulated CSP-like reaction was associated with the shedding of proteinaceous material in the molecular weight size range of from 1200–1700 kDa when measured by SDS polyacrylamide gel electrophoresis. As indicated by the findings presented in the following Example, we discovered that the shed proteinaceous material contained an epitope that was specifically bound by mAb 3E2. Thus, the antigenic target of a mAb having the ability to induce the CSP-like reaction in sporozoites of C. parvum was localized to high molecular weight material shed during the CSP-like reaction.

Example 14 describes the methods used to demonstrate that the epitope recognized by mAb 3E2 was expressed on different developmental stages of C. parvum and that this material was shed during the CSP-like reaction. The molecular species bound by mAb 3E2 during the CSP-like reaction, from among the multiple bands recognized by mAb 3E2 in whole sporozoites is referred to below as the CSL protein.

EXAMPLE 14

The CSL Protein Shed from Sporozoites After the CSP-Like Reaction is also Present in Excysted Oocysts and Whole Sporozoites

Membranous material released from approximately $9 \times 10^7$ sporozoites after the mAb 3E2-induced CSP-like reaction was isolated by PERCOLL density gradient centrifugation as described in the preceding Example. The material was washed and electrophoretically separated on a 2–12% SDS polyacrylamide gel under reducing conditions. Bioreactor-derived (serum free), purified mAb 3E2 (15 μg), purified sporozoites ($3-7.5 \times 10^6$), sporozoite antigen purified by mAb C4A1 affinity chromatography (2 μg purified protein), and the soluble phase of a viable sporozoite culture supernatant (2 μg protein) harvested by ultracentrifugation (100,000×g, 1 hour) and filtration (0.2 μm pore size) after two hours of incubation in the absence of mAb, were electrophoresed and silver stained for comparison. All preparations were solubilized in lysis buffer containing protease inhibitors prior to electrophoresis. Molecular weight standards used were titin (2,450 kDa); nebulin (770 kDa); and myosin (208 kDa).

Results indicated that a prominent *C. parvum* derived band having a molecular weight of approximately 1,400 kDa was present in purified membranous precipitates shed during the CSP-like reaction. This band, which represented the CSL high molecular weight exoantigen, co-migrated with a band of the same molecular weight derived from (1) purified whole sporozoites, (2) mAb C4A1 affinity chromatography purified sporozoite antigen (containing a subset of whole sporozoite bands), and (3) the soluble phase of viable sporozoite culture supernatant. Several other lower molecular weight bands present in the membranous precipitate preparation co-migrated with bands of similar molecular weight derived from purified mAb 3E2, indicating that they were of nonsporozoite origin (mAb heavy and light chains). The results also indicated that the high molecular weight CSL antigen which harbored the mAb 3E2 binding site was the major band in both PERCOLL-purified precipitates and soluble phase of sporozoite culture supernatant. These findings indicated that the antigenic target of mAb 3E2 specifically involved in the CSP-like reaction had been identified and purified and was constitutively released by sporozoites in culture.

As described in the following Example, Western blotting demonstrated that a single species having a molecular weight of approximately 1400 kDa and immunoreactive with mAb 3E2 was present in PERCOLL gradient-isolated membranous precipitate shed from viable sporozoites after the CSP-like reaction. The high molecular weight species was the only reactive band in precipitates derived from sporozoites. This species corresponded in size to the 1400 kDa protein band observed in silver-stained gels and was immunoreactive with both mAbs 3E2 and C4A1. This band co-migrated with an immunoreactive band of the same molecular weight that was present among a collection of immunoreactive bands in solubilized whole sporozoite preparations.

Example 15 describes the methods used to demonstrate that mAb 3E2 binds the CSL glycoprotein antigen directly.

EXAMPLE 15

The CSL Glycoprotein Harbors the Epitope Recognized by mAb 3E2

Solubilized sporozoites or shed precipitates were resolved by reducing SDS-PAGE in a 2–12% gradient gel and blotted onto a nitrocellulose membrane. A control lane was loaded with 25 μg mAb 3E2 alone. Lanes were probed with mAb 3E2, mAb C4A1 or an isotype control mAb. Affinity-purified, alkaline phosphatase-conjugated goat anti-mouse IgM antibody was used to detect binding following addition of substrate.

Results indicated that the only immunoreactive bands other than the 1400 kDa band in lanes containing purified membranous precipitates co-migrated with mouse mAb IgM bands, and therefore represented mAb 3E2 components in shed material. Immunoreactive, parasite-derived low molecular weight bands in PERCOLL-purified precipitates, which may not have been visualized in Western blots of 2–12% gels, were not detected in Western blots of purified precipitates resolved in 10–20% gels. The results indicated that the approximately 1400 kDa band was the only antigen bound by mAb 3E2 during the CSP-like reaction, and therefore must be mechanistically involved in the reaction. mAb C4A1, which did not elicit the CSP-like reaction, recognized an epitope on the approximately 1400 kDa antigen different from the epitope recognized by mAb 3E2.

As described in the following Example, a two-site immunoradiometric assay (IRMA) was employed to confirm that the epitope disposed on the high molecular weight target antigen of mAb 3E2 was repetitive. This feature of the epitope recognized by mAb 3E2 advantageously facilitated immunoprecipitation of the target antigen by the mAb in the absence of a secondary antibody.

Example 16 describes the method used to confirm that the epitope recognized by mAb 3E2, and disposed on the high molecular weight CSL antigen, was a repetitive epitope.

EXAMPLE 16

The Epitope Disposed on the CSL Glycoprotein and Recognized by mAb 3E2 is Repetitive

Two-site IRMA was carried out according to the method described by Cochrane et al. in *Infect. Immun.* 45:592 (1984), with the following modifications. Removable Immulon 4 wells in microtiter plate frames (Dynatech, Chantilly, Va.) were coated for 12 hours (4° C.) with purified mAb 3E2 or purified IgM control mAb of irrelevant specificity diluted in PBS (25 μg mAb/ml final concentration), washed, blocked (2% [w/v] BSA in PBS), and washed again, all according to standard laboratory methods. Constitutively released CSL high molecular weight exoantigen was obtained for analysis by incubating purified viable sporozoites in Hank's buffered saline solution (HBSS) for 2 hours (37° C.). The preparation was then cooled to 4° C. and centrifuged at 5000×g for 10 minutes (4° C.) to remove sporozoites. The exoantigen-containing supernatant was ultracentrifuged at 100,000×g for 20 minutes (4° C.) and passed through a syringe-tip filter having a 0.2 μm pore size to remove residual insoluble material. Following the addition of protease inhibitors phenylmethylsulfonyl fluoride, N-tosyl-L-lysl chloromethyl ketone, and iodoacetamide, samples were stored frozen at −80° C. until use.

The CSL high molecular weight soluble exoantigen released from $8 \times 10^6$ viable sporozoites was added to each of ten replicate mAb 3E2- or control IgM mAb-coated wells in 200 μl PBS and incubated 2 hours (37° C.). Free antigen was removed by washing, and wells were then incubated with $^{125}$I-labeled mAb 3E2 (2×10$^5$ TCA precipitable cpm/well) for 1 hour at 37° C. After washing, $^{125}$I-labeled mAb 3E2 specifically bound to CSL high molecular weight exoantigen which had been immobilized to the mAb 3E2-coated wells. Immobilized radioactivity was quantitated as "counts per minute" (cpm) using a gamma counter. Results indicated that 54,317±2148 cpm (n=10) of radiolabeled mAb 3E2 was immobilized for mAb 3E2 coated wells but only 2823±186 cpm (n=10) was immobilized for wells coated with the IgM control mAb. These results indicated that the epitope recognized by mAb 3E2 occurred at least twice on the CSL high molecular weight exoantigen that was mechanistically involved in the CSP-like reaction.

Constitutive release of the CSL high molecular weight exoantigen from sporozoites was demonstrated by immunoprecipitation of the radioiodinated soluble phase of viable sporozoite culture supernatant by mAb 3E2-Sepharose, SDS-PAGE, and autoradiography. Results from these procedures indicated that mAb 3E2 specifically precipitated a single, prominent, approximately 1400 kDa radioiodinated antigen from the soluble phase of cultured sporozoites as revealed by resolution of immunoprecipitated material in reducing 2–12% SDS-PAGE followed by autoradiography. Control mAb IgM-Sepharose of irrelevant specificity did not precipitate this antigen. Further, silver stained SDS-PAGE reducing gels of the soluble phase of sporozoite culture supernatant contained a major, approximately 1400 kDa band, substantially free of other proteins.

Example 17 describes a method useful for purifying the high molecular weight CSL antigen that was involved in the CSP-like reaction and that was recognized by mAb 3E2.

EXAMPLE 17

Isoelectric Focussing Method of Purifying the High Molecular Weight Antigen Mechanistically Involved in the CSP-Like Reaction Excysted oocysts were solubilized by freeze-thaw and sonication in the presence of protease inhibitors and 1% w/v octyl glucoside. The soluble fraction was collected by centrifugation at 5000×g for 10 minutes (4° C.) and dialyzed for 12 hours against distilled water using a 12,000–14,000 molecular weight cut-off membrane. A Rotofor (Bio-Rad) isoelectric focusing chamber was then used to isolate the high molecular weight exoantigen from the solubilized, dialyzed sporozoite preparation. The Rotofor apparatus was prepared by addition of 0.1 M phosphoric acid (pH 1.2) to the cationic chamber, addition of 0.1 M NaOH (pH 12.0) to the anionic chamber, and addition of HPLC-quality water containing 3% ampholines (pH 3.5–5.0 range) to the focussing chamber. The apparatus was maintained at 4° C. and connected to a 12-watt power source for 1 hour to establish a pH gradient. The solubilized, dialyzed sporozoite preparation (2 ml) was then added and isoelectric focussing allowed to proceed for 6 hour at 12 watts. At the completion of the focussing cycle, 20 fractions spanning the separated protein range were collected, neutralized, and analyzed for presence and purity of the high molecular weight antigen by Western blotting and SDS-PAGE/silver staining. Refocusing of fractions containing the high molecular weight antigen were performed until immunoreactive, pure antigen was obtained.

The results of these procedures demonstrated that the exoantigen target of mAb 3E2 could be isolated from all other sporozoite antigen species, including those recognized by mAb 3E2, and that the purification procedures employed in this process did not destroy immunoreactivity of the antigen. More particularly, a silver stained 2–12% gradient SDS-PAGE reducing gel of solubilized *C. parvum* before isoelectric focussing revealed the presence of greater than 50 bands in the 7–2,450 kDa range, including the CSL high molecular weight exoantigen. After isoelectric focusing, a single band having a molecular weight of approximately 1,400 kDa was visualized by silver staining 2–12% SDS-PAGE gels of purified antigen. Western blotting of the purified sample demonstrated a single, approximately 1,400 kDa band immunoreactive with mAb 3E2. The purified antigen co-migrated with an antigen of the same molecular weight from among the multiple antigens recognized by mAb 3E2 in whole *C. parvum* preparations.

As described in the following Example, purified CSL glycoprotein reactive with mAb 3E2 and isolated from oocysts by preparative SDS-PAGE was shown to function as an immunogen capable of stimulating an anti-*C. parvum* response in an animal. While the Example describes a particular protocol, alternative immunization protocols also are expected to be useful for stimulating an anti-*C. parvum* immune response in an animal. For example, we contemplate that adjuvants familiar to those having ordinary skill in the art can be administered in combination with antigen to stimulate vigorous anti-*C. parvum* immune responses. A particular protocol useful for immunizing cows and other ruminants can be found in *Infect. Immun.* 62:1927 (1994). According to this protocol antigen is combined with Ribi TDM-CWS adjuvant (Ribi Immunochem Research, Hamilton, Mont.) and administered subcutaneously (in the shoulder) and intramuscularly (in the hip) at timed intervals. This protocol is particularly useful for stimulating the production of hyperimmune colostrum useful for conferring passive immunity in calves and humans when the colostrum is administered orally. The carrier used for dispersing the purified antigen of the invention can be a buffered saline solution, such as phosphate buffered saline, and optionally can include an adjuvant such as Freund's adjuvant or the Ribi adjuvant. Other commercially available adjuvants also are contemplated for use with the invention to stimulate a strong anti-*C. parvum* immune response. If the purified antigen is a weak immunogen in a particular application, then the antigen can be coupled to a carrier protein such as keyhole limpet hemocyanin to improve the immunogenicity of the purified CSL glycoprotein shown herein to be immunoreactive with mAb 3E2.

Example 18 describes the method that was used to stimulate active immunity in an animal. While the Example makes explicit reference to immunization of a chicken, the method is equally adaptable to immunization of other animals, including mammals.

EXAMPLE 18

Method of Stimulating an Anti-*C. parvum* Immune Response in an Animal

CSL glycoprotein was purified from oocysts by preparative SDS polyacrylamide gel electrophoresis. SDS-PAGE and silver staining was used to confirm purity of the CSL glycoprotein sample. Western blot analysis confirmed that reactivity of CSL with mAb 3E2 was preserved following the purification procedure. Chickens were hyperimmunized with the purified CSL glycoprotein according to standard methods. More particularly, the purified CSL glycoprotein antigen was combined with Freund's complete adjuvant and administered subcutaneously and intramuscularly for the first immunization at approximately two months of age. The combination of antigen and Freund's incomplete adjuvant was administered subcutaneously and intramuscularly at four week intervals for between 5 and 7 rounds of immunization. Each immunization consisted of 1 ml total volume and was split equally between the subcutaneous and intramuscular injections. Serum antibody responses in the hyperimmunized chickens were monitored by indirect immunofluorescence and Western blotting, as described above.

Results of these procedures indicated that chickens hyperimmunized with the purified CSL glycoprotein advantageously exhibited high titers of serum antibodies directed against sporozoites. Western blotting procedures indicated that the anti-CSL antibodies were present in serum samples isolated from the hyperimmunized chickens. Interestingly, the chickens also developed antibody responses against multiple, lower molecular weight sporozoite antigens. This latter finding indicated the presence of cross-reactive epitopes on the CSL glycoprotein used as an immunogen and the lower molecular weight species. Importantly, the anti-CSL sera from the hyperimmunized chickens was also shown to induce the CSP-like reaction in live sporozoites.

These results clearly indicated that an immunogenic composition which included a substantially purified *C. parvum* antigen specifically recognizable by mAb 3E2 and a pharmaceutically acceptable carrier had utility in a method for stimulating an anti-*C. parvum* immune response in an animal. The method of stimulating an anti-*C. parvum* immune response involved obtaining the immunogenic composition and administering the immunogenic composition to the animal according to a vaccination protocol. Pharmaceutically acceptable carriers such as saline solutions, optionally including one or more adjuvants, could be co-injected with the CSL antigen to aid in delivery of the immunogen and in stimulating a vigorous immune response.

Example 19 describes one method of stimulating an active immune response against *C. parvum* based on immunization with the CSL constituent of the GP25-200 complex. Although this Example describes the vaccination of a human subject, the method can also be adapted for use in immunizing animals, such as cattle or other livestock. Those having ordinary skill in the art will recognize that other methods for performing a vaccination are well known and can be used in connection with the purified high molecular weight CSL antigen constituent of the GP25-200 complex.

EXAMPLE 19

Vaccine Composition Comprising the CSL Glycoprotein

A human subject at risk of exposure to *C. parvum* is first identified. The subject is injected subcutaneously with an immunogenic composition comprising purified CSL high molecular weight antigen reactive with mAb 3E2, wherein the antigen is produced in accordance with the method of Examples 17 and 18. During preparation of the immunogenic composition, a sample containing the purified CSL high molecular weight antigen is first dialyzed against physiological saline, filter-sterilized, concentrated and combined with a pharmaceutically acceptable carrier. An adjuvant may optionally be included in the composition. Injection is repeated once every three weeks for a total of four injections. Immunizing doses of the immunogenic composition are determined by methods that will be appreciated by those having ordinary skill in the art. Stimulation of an immune response in the patient is monitored by standard techniques, such as ELISA. Serum isolated from a blood sample twelve weeks after the first injection of the immunogenic composition is found to contain a high concentration of antibodies reactive with *C. parvum* as detected by indirect immunofluorescence staining. In contrast, a serum sample obtained from the same patient prior to the first injection of the immunogenic composition showed substantially no antibodies reactive with *C. parvum*. This indicates that the patient has developed an immune response against *C. parvum* as a result of having been administered with an immunogenic composition comprising the purified CSL high molecular weight glycoprotein antigen reactive with mAb 3E2. The same patient does not develop diarrhea when challenged with live *C. parvum* administered orally. This latter observation proves that immunization with a composition comprising the purified CSL high molecular weight glycoprotein antigen reactive with mAb 3E2 confers protective immunity against infection with *C. parvum*.

What is claimed is:

1. Monoclonal antibody 3E2 secreted by hybridoma ATCC HB 12075.

2. A hybridoma having ATCC accession number ATCC HB 12075 and secreting monoclonal antibody 3E2.

3. A pharmaceutical composition for administration to a mammal, comprising:

a monoclonal antibody 3E2 secreted by hybridoma ATCC HB 12075, at least one stabilizing agent, and a pharmaceutically acceptable carrier.

4. The pharmaceutical composition of claim 3, wherein the stabilizing agent is selected from the group consisting of protease inhibitors, carrier proteins and pH buffering agents.

5. A pharmaceutical composition suitable for administration to a mammal, comprising a monoclonal antibody 3E2 secreted by hybridoma ATCC HB 12075 and at least one other anti-*Cryptosporidium parvum* monoclonal antibody, in a pharmaceutically acceptable carrier.

6. The pharmaceutical composition of claim 5, wherein at least one said other anti-*Cryptosporidium parvum* monoclonal antibody does not share an epitope binding specificity with monoclonal antibody 3E2.

7. The pharmaceutical composition of claim 6, wherein said at least one said other anti-*Cryptosporidium parvum* monoclonal antibody binds to an antigen selected from the group consisting of GP25-200, GP23, and CPS-500.

8. The pharmaceutical composition of claim 7, which comprises at least one monoclonal antibody that binds to GP25-200 or at least one monoclonal antibody that binds to GP23.

9. The pharmaceutical composition of claim 6, which comprises at least one monoclonal antibody that binds to GP25-200 and at least one monoclonal antibody that binds to GP23.

10. The pharmaceutical composition of claim 7, which comprises at least one monoclonal antibody that binds to GP25-200.

11. The pharmaceutical composition of claim 7, which comprises at least one monoclonal antibody that binds to GP23.

12. The pharmaceutical composition of claim 7, which comprises at least one monoclonal antibody that binds to CPS-500.

13. The pharmaceutical composition of claim 7, which comprises at least one monoclonal antibody that binds to GP25-200, at least one monoclonal antibody that binds to GP23 and at least one monoclonal antibody that binds to CPS-500.

14. The pharmaceutical composition of claim 5, further comprising mammalian colostrum, and, optionally, said colostrum comprises antibodies to *Cryptosporidium parvum*.

15. The pharmaceutical composition of claim 6, further comprising mammalian colostrum, and, optionally, said colostrum comprises antibodies to *Cryptosporidium parvum*.

16. The pharmaceutical composition of claim 7, further comprising mammalian colostrum, and, optionally, said colostrum comprises antibodies to *Cryptosporidium parvum*.

17. The pharmaceutical composition of claim 5, further comprising at least one stabilizing agent.

18. The pharmaceutical composition of claim 17, wherein the stabilizing agent is selected from the group consisting of protease inhibitors, carrier proteins and pH buffering agents.

19. The pharmaceutical composition of claim 6, further comprising at least one stabilizing agent.

20. The pharmaceutical composition of claim 19, wherein the stabilizing agent is selected from the group consisting of protease inhibitors, carrier proteins and pH buffering agents.

21. The pharmaceutical composition of claim 7, further comprising at least one stabilizing agent.

22. The pharmaceutical composition of claim 21, wherein the stabilizing agent is selected from the group consisting of protease inhibitors, carrier proteins and pH buffering agents.

23. The pharmaceutical composition of claim 14, wherein said mammalian colostrum is bovine colostrum.

* * * * *